United States Patent [19]

Fukumoto et al.

[11] Patent Number: 5,714,649
[45] Date of Patent: Feb. 3, 1998

[54] 1-HALO-CIS-3-TETRADECENES AND PROCESSES FOR THE PREPARATION OF CIS-OLEFIN COMPOUNDS BY USING SAME

[75] Inventors: Takehiko Fukumoto; Daisuke Iwai; Shigeo Okano; Hiroshi Suzuki; Mitsuyoshi Oshima, all of Joetsu, Japan

[73] Assignee: Shin-Etsu Chemical CO., Ltd., Tokyo, Japan

[21] Appl. No.: 575,333

[22] Filed: Dec. 20, 1995

Related U.S. Application Data

[60] Continuation of Ser. No. 423,167, Apr. 17, 1995, abandoned, which is a division of Ser. No. 274,139, Jul. 12, 1994, Pat. No. 5,463,149.

[30] Foreign Application Priority Data

Jul. 20, 1993 [JP] Japan ................................ 178694/1993

[51] Int. Cl.$^6$ .................................................. C07C 19/08
[52] U.S. Cl. ............................ 570/135; 585/612; 585/620
[58] Field of Search ............................ 570/135; 585/612, 585/620

[56] References Cited

PUBLICATIONS

Chemical Abstracts vol. 77 (15) p. 97 695f(1972).
Chemical Abstracts vol. 86 (21)p. 155 133u(1976).
Chemical Abstracts, vol. 110 (9) 75093f (1989).
Chemical Abstracts, vol. 116, No. 151356 and IZV Akad. Nauk. SSSR, Ser. Khim (1991) (3), 640–4.
Chemical Abstracts, vol. 118, No. 59449, and Tetrahedron Letters Vol. 33, No. 43, pp. 6411–6414 (1992).
Derwent Abstract No. 87–302843 and JP 62–212347 (1987).
Derwent Abstract No. 91–263831 and JP 3–173849 (1991).
Derwent Abstract No. 87–351010 and JP 62–252738 (1987).
Ivanova et al; Izv.Akad.Nauk SSSR, Ser.Khim.(3),640–4 (1991).
Keinen et al; Tetrahedron Lett. 33(43),6411–14 (1992).
Chemical Abstract Search report . . . Apendix A (1997).
Derwent Abstract No. 87–302843 and JP 62–212347 (Mar. 12, 1986).
Chemical Abstracts; vol. 78, No. 84127t; Kovalev et al (1973).
Organic Chemistry; Hendrickson et al ; pp. 127 and 464–468 (1970).

*Primary Examiner*—C. Warren Ivy
*Assistant Examiner*—Sreeni Padmanabhan
*Attorney, Agent, or Firm*—McAulay Fisher Nissen Goldberg & Kiel, LLP

[57] ABSTRACT

Disclosed are compounds suitable for use as raw materials which enable cis-olefin compounds useful as physiologically active substances such as the sex pheromones of various insects, or as intermediates for the synthesis thereof to be prepared on an industrial scale at a reasonable cost, and processes for the preparation of cis-olefin compounds by using the same. For this purpose, novel compounds (i.e., 1-halo-cis-3-tetradecenes) of the general formula (I)

$$CH_3(CH_2)_9CH=CH(CH_2)_2X \qquad (I)$$

wherein X is a halogen atom, are used as raw materials for the preparation of cis-olefin compounds.

2 Claims, 6 Drawing Sheets

1-HALO-CIS-3-TETRADECENES AND PROCESSES FOR THE PREPARATION OF CIS-OLEFIN COMPOUNDS BY USING SAME

This is a continuation of application Ser. No. 08/423,167 filed Apr. 17, 1995, now abandoned, which, in turn, is a divisional of Ser. No. 08/274,139 filed Jul. 12, 1994; now U.S. Pat. No. 5,463,149.

FIELD OF THE INVENTION AND RELATED ART STATEMENT

This invention relates to processes for the preparation of cis-olefin compounds useful as physiologically active substances such as the sex pheromones of various insects, or as intermediates for the synthesis thereof. In particular, it relates to 1-halo-cis-3-tetradecenes and processes for the preparation of cis-olefin compounds by using the same.

As an example of the art concerning the preparation of cis-olefin compounds useful as physiologically active substances such as the sex pheromones of various insects, or as intermediates for the synthesis thereof, a variety of processes for preparing an intermediate (2-methyl-cis-7-octadecene) for the synthesis of the sex pheromone [cis-7,8-epoxy-2-methyloctadecene (racemate)] of the gypsy moth (*Lymantria dispar* L.) have conventionally been known. These processes can be roughly divided into the following three classes:

(1) A process for preparing the cis-olefin compound by converting an 1-alkyne into a metal acetylide, reacting the metal acetylide with an alkyl halide, and subjecting the resulting alkynyl compound to catalytic reduction (Chemical Abstracts 112(23)216209d, 110(9)75093f, 93(17)167560q, 78(13)84127t, etc.).

(2) A process for preparing the cis-olefin compound by utilization of the Wittig reaction (Chemical Abstracts 109(13)110058b, 99(7)53420n, 86(7)43458y, 77(15)97695f, etc.).

(3) A process for preparing the cis-olefin compound by way of an organosilicon intermediate (Chemical Abstracts 86(21)155133v).

However, the above-described prior art processes have the following disadvantages:

In the process of class (1), an expensive and hard-to-handle material such as n-butyl lithium is used. Moreover, it is necessary to use a material suspected of carcinogenicity, such as HMPT (hexamethylphosphoric triamide).

In the process of class (2), the Wittig reaction has low stereoselectivity for cis-isomers, so that trans-isomers tend to be formed as by-products on an appreciable level.

In the process of class (3), very special raw materials are used. This requires considerable expenses for the preparation thereof.

Thus, there has been no efficient process for preparing an intermediate for the synthesis of the sex pheromone of the gypsy moth. This also applies generally to cis-olefin compounds useful as physiologically active substances such as the sex pheromones of various insects, or as intermediates for the synthesis thereof.

Under these circumstances, there has been a demand for a technique which enables such cis-olefin compounds to be prepared on an industrial scale at a reasonable cost.

OBJECT AND SUMMARY OF THE INVENTION

Accordingly, it is an object of the present invention to provide compounds suitable for use as raw materials which enable cis-olefin compounds to be prepared on an industrial scale at a reasonable cost, and processes for the preparation of cis-olefin compounds by using the same.

The present inventors have made extensive investigations on the preparation of cis-olefin compounds useful as physiologically active substances such as the sex pheromones of various insects, or as intermediates for the synthesis thereof. As a result, 1-halo-cis-3-tetradecenes having the general formula (I)

$$CH_3(CH_2)_9CH=CH(CH_2)_2X^a \qquad (I)$$

wherein $X^a$ is a halogen atom, have been developed as novel compounds suitable for use as raw materials for the preparation of such cis-olefin compounds.

According to a first aspect of the present invention, the above-described object is accomplished by a compound (i.e., 1-halo-cis-3-tetradecene) having the general formula (I)

$$CH_3(CH_2)_9CH=CH(CH_2)_2X^a \qquad (I)$$

wherein $X^a$ is a halogen atom.

According to a second aspect of the present invention, the above-described object is accomplished by a novel compound (i.e., 1-halo-cis-3-tetradecene) suitable for use as a raw material for the preparation of cis-olefin compounds, the compound having the general formula (I)

$$CH_3(CH_2)_9CH=CH(CH_2)_2X^a \qquad (I)$$

wherein $X^a$ is a halogen atom.

According to a third aspect of the present invention, the above-described object is accomplished by a process for the preparation of cis-olefin compounds which comprises converting a 1-halo-cis-3-tetradecene into an organometallic compound of the general formula (II)

$$CH_3(CH_2)_9CH=CH(CH_2)_2M^a \qquad (II)$$

wherein $M^a$ is a metal atom or $MgX^a$ in which $X^a$ is a halogen atom, and reacting the organometallic compound with a compound of the general formula RY wherein R is an alkyl group and Y is a bromine atom, iodine atom, tosyloxy group or mesyloxy group, to form a cis-olefin compound of the general formula (III)

$$CH_3(CH_2)_9CH=CH(CH_2)_2R \qquad (III)$$

wherein R is as previously defined.

According to a fourth aspect of the present invention, the above-described object is accomplished by a process for the preparation of cis-olefin compounds which comprises converting a compound of the general formula $RX^b$ wherein R is an alkyl group and $X^b$ is a halogen atom, into an organometallic compound $RM^b$ wherein $M^b$ is a metal atom or $MgX^b$, and reacting the organometallic compound $RM^b$ with a compound of the general formula (IV)

$$CH_3(CH_2)_9CH=CH(CH_2)_2Z \qquad (IV)$$

wherein Z is a bromine or iodine atom, to form a cis-olefin compound of the general formula (V)

$$CH_3(CH_2)_9CH=CH(CH_2)_2R \qquad (V)$$

wherein R is as previously defined.

The present invention makes it possible to use raw materials which have low toxicity and are easy to handle, and thereby obtain cis-olefin compounds while securing a high purity of the cis-isomers without difficulty. Thus, cis-olefin compounds can be prepared on an industrial scale at a reasonable cost.

DETAILED DESCRIPTION OF THE PREFERRED EMBODIMENTS

As described above, the present inventors have developed 1-halo-cis-3-tetradecenes having the general formula (I)

$$CH_3(CH_2)_9CH\!\!=\!\!CH(CH_2)_2X^a \qquad (I)$$

wherein $X^a$ is a halogen atom, as novel compounds suitable for use as raw materials for the preparation of cis-olefin compounds useful as physiologically active substances such as the sex pheromones of various insects, or as intermediates for the synthesis thereof.

When the halogen atom $X^a$ is Cl, Br or I, the boiling point of this compound is as follows:

| | |
|---|---|
| $X^a$ = Cl | 123–125° C./3 mmHg |
| = Br | 133–136° C./3 mmHg |
| = I | 116–117° C./0.2 mmHg |

Each of these halides is a pale-yellow oily liquid.

These halides can readily be prepared by halogenating the well-known compound cis-3-tetradecen-1-ol (Chemical Abstracts Registry Number 68892-27-3) of formula (VI)

$$CH_3(CH_2)_9CH\!\!=\!\!CH(CH_2)_2OH \qquad (VI)$$

1-halo-cis-3-tetradecenes can be obtained by halogenating the above alcohol according to a halogenation procedure using, for example, a phosphorus halide, triphenylphosphine-tetrahalogenated hydrocarbon, sulfonyl halide, sulfonic ester or thionyl halide.

Some examples of such halogenation procedures are represented by the following scheme:

Process 1 for the Preparation of cis-Olefin Compounds

Now, a process (according to the third aspect of the present invention) for the preparation of cis-olefin compounds by using one of the above-described 1-halo-cis-3-tetradecenes as a raw material (or as a starting material or intermediate) is described below.

In this process, a 1-halo-cis-3-tetradecene is first converted into an organometallic compound of the general formula (II)

$$CH_3(CH_2)_9CH\!\!=\!\!CH(CH_2)_2M^a \qquad (II)$$

wherein $M^a$ is a metal atom or $MgX^a$ in which $X^a$ is a halogen atom.

The metal atom $M^a$ can be, for example, lithium. When $M^a$ is $MgX^a$, the organometallic compound represents a Grignard reagent. Since the reaction of lithium with a 1-halo-cis-3-tetradecene requires delicate reaction conditions, the preparation of a Grignard reagent is more practical.

The organometallic compound of the general formula (II) can be obtained by adding a 1-halo-cis-3-tetradecene solution (dropwise) to a solvent containing pieces of a metal used as a raw material.

The amount of metal used as a raw material is 1.7 to 2.0 equivalents for lithium and 1.0 to 1.2 equivalents for magnesium, per mole of the 1-halo-cis-3-tetradecene. The solvent for the 1-halo-cis-3-tetradecene solution may preferably be diethyl ether, tetrahydrofuran or the like. The reaction temperature is in the range of 0° to 40° C. for lithium and 50° to 90° C. for magnesium.

Next, the organometallic compound of the general formula (II) is reacted with a compound of the general formula RY.

In the general formula RY, R is an alkyl group and Y is a bromine atom, iodine atom, tosyloxy group (—OSO$_2$Ph) or mesyloxy group (—OSO$_2$CH$_3$). Specific examples of the compound RY include alkyl bromides and alkyl iodides such as ethyl bromide (or iodide), n-heptyl bromide (or iodide), isoamyl bromide (or iodide) and n-undecyl bromide (or iodide); isoamyl p-toluenesulfonate; and n-hexyl methanesulfonate.

As the solvent, diethyl ether, tetrahydrofuran or the like may preferably be used. In some cases, DMF (N,N-dimethylformamide), DMI (N,N-dimethylimidazolidinone) or the like may also be used as an assistant.

For example, when the organometallic compound of the general formula (II) is a Grignard reagent, it is preferable to use a copper catalyst (e.g., a monovalent or divalent copper halide such as $Cu(I)X^c$ or $Cu(II)X^c_2$) in an amount of 0.001 to 0.1 molar equivalent per mole of the Grignard reagent.

The reaction is carried out by dissolving the compound RY in a solvent and adding the organometallic compound of the general formula (II), in an amount of 1.0 to 1.1 moles per mole of the compound RY, dropwise thereto at a temperature of −40° to 30° C. in the presence of a catalyst.

Process 2 for the Preparation of cis-Olefin Compounds

Now, a process (as claimed in claim 4) for the preparation of cis-olefin compounds by converting an alkyl halide $RX^b$ into an organometallic compound $RM^b$ and reacting the latter with 1-halo-cis-3-tetradecene is described below.

In this process, an alkyl halide $RX^b$ is converted into an organometallic compound $RM^b$.

In the general formula $RX^b$, R is an alkyl group and $X^b$ is a halogen atom. Specific examples of the alkyl halide $RX^b$ include alkyl bromides and alkyl iodides such as ethyl bromide (or iodide), n-heptyl bromide (or iodide), isoamyl bromide (or iodide) and n-hexyl bromide (or iodide). This compound $RX^b$ is converted into an organometallic compound $RM^b$ wherein $M^b$ is a metal atom or $MgX^b$) which can be an alkyl lithium or a Grignard reagent. The metal atom $M^b$ can be, for example, lithium.

This conversion is carried out by reacting the alkyl halide $RX^b$ with pieces of a metal (e.g., Li or Mg) in a solvent such as diethyl ether or tetrahydrofuran.

Next, the resulting organometallic compound $RM^b$ is reacted with a compound (1-halo-cis-3-tetradecene) of the general formula (IV)

$$CH_3(CH_2)_9CH\!=\!\!CH(CH_2)_2Z \qquad (IV)$$

wherein Z is a bromine or iodine atom.

Thus, there can be obtained a cis-olefin compound of the general formula (V)

$$CH_3(CH_2)_9CH\!=\!\!CH(CH_2)_2R \qquad (V)$$

wherein R is as previously defined.

When the organometallic compound $RM^b$ is an alkyl lithium, this alkyl lithium is reacted with cuprous iodide to form a dialkyl copper lithium (or lithium organocuprate), which is then reacted with a 1-halo-cis-3-tetradecene.

When the organometallic compound $RM^b$ is a Grignard reagent, it is common practice to react the Grignard reagent with a 1-halo-cis-3-tetradecene in the presence of a copper catalyst (e.g., a monovalent or divalent copper halide such as $Cu(I)X^c$ or $Cu(II)X^c_2$) used in an amount of 0.001 to 0.1 molar equivalent per mole of the Grignard reagent.

When a lithium organocuprate is used, not only 0.5 equivalent of the alkyl group is wasted, but also the organometallic compound has low stability. Consequently, the use of a Grignard reagent is preferred.

After completion of the reaction, the cis-olefin compound so formed is poured into water and isolated according to any of conventional separation techniques such as distillation and column chromatography. Thus, the desired cis-olefin compound can be obtained without reducing the geometrical purity of the 1-halo-cis-3-tetradecene.

According to the present invention, various cis-olefin compounds having physiological activities can be prepared in the above-described manner. With regard to insects, examples of such cis-olefin compounds are given in Table 1 below.

TABLE 1

| cis-Olefin compound | Physiological activity |
|---|---|
| $CH_3(CH_2)_9CH\!=\!\!CH(CH_2)_3CH_3$ cis-5-Hexadecene | The copulation-inhibiting substance of the rice stem borer |
| $CH_3(CH_2)_9CH\!=\!\!CH(CH_2)_8CH_3$ cis-10-Henicosene | A sex pheromone component of *Drosophila virlis* |
| $CH_3(CH_2)_9CH\!=\!\!CH(CH_2)_7CH_3$ cis-9-Icosene | The response-stimulating substance of *Drosophila virlis* |
| $CH_3(CH_2)_9CH\!=\!\!CH(CH_2)_4CH(CH_3)_2$ 2-Methyl-cis-7-octadecene | A sex pheromone precursor of the gypsy moth An attraction inhibitor |
| $CH_3(CH_2)_9CH\!=\!\!CH(CH_2)_{12}CH_3$ cis-11-Pentaicosene | A sex pheromone component of *Drosophila virlis* |

The present invention is further illustrated by the following examples. However, these examples are not to be construed to limit the scope of the invention.

EXAMPLE 1

Synthesis of 1-chloro-cis-3-tetradecene (a compound in accordance with the present invention)

395 g (1.86 moles) of cis-3-tetradecen-1-ol, 680 g of dichloromethane and 186 g (1.84 moles) of triethylamine were placed in a 3-liter reactor and cooled to 0° C. Then, 237 g (1.99 moles) of thionyl chloride was added dropwise thereto so that the temperature did not exceed 40° C. This mixture was stirred for an hour and then reacted for 2 hours under reflux of dichloromethane. After completion of the reaction, 600 g of purified water was added and the resulting mixture was allowed to separate into two layers. The organic layer was recovered, washed with 600 g of a 5% aqueous NaOH solution and then 500 g of a 5% sodium chloride solution, freed of solvent, and distilled to obtain 385 g of an oily liquid having a boiling point of 123°–125° C./3 mmHg. On the basis of various spectral data, this product was identified as 1-chloro-cis-3-tetradecene (purity 96%, yield 86.1%).

EXAMPLE 2

Synthesis of 1-bromo-cis-3-tetradecene (a compound in accordance with the present invention)

21.2 g (0.1 mole) of cis-3-tetradecen-1-ol and 30 g of tetrahydrofuran were placed in a 1-liter reactor, and CBr4 (36 g, 0.11 mole) dissolved in 20 ml of tetrahydrofuran was added dropwise thereto at room temperature. Then, 30 g (0.115 mole) of triphenylphosphine dissolved in 30 ml of tetrahydrofuran was added dropwise thereto so that the temperature did not exceed 40° C., and this mixture was stirred at room temperature for an hour. After completion of the reaction, 10 ml of methanol was added and the resulting mixture was stirred for several minutes. The solvent was removed under reduced pressure and the residue was extracted with n-hexane. After the triphenylphosphine in the hexane layer was filtered off, the resulting hexane layer was distilled to obtain 25 g of a pale-yellow oily liquid having a boiling point of 133°–136° C./3 mmHg. On the basis of various spectral data, this product was identified as 1-bromo-cis-3-tetradecene (purity 96%, yield 91%).

EXAMPLE 3

Synthesis of 1-iodo-cis-3-tetradecene (a compound in accordance with the present invention)

21.2 g (0.1 mole) of cis-3-tetradecen-1-ol, 200 ml of dichloromethane and 104 g (1.03 moles) of triethylamine were placed in a 1-liter reactor and cooled to 0° C. Then, 12 g (0.105 mole) of methanesulfonyl chloride was added dropwise thereto. After this mixture was stirred at room temperature for an hour, 200 ml of cold water was added and the resulting mixture was allowed to separate into two layers. The dichloromethane layer was recovered and dried by the addition of 3 g of anhydrous sodium sulfate, followed by rapid removal of the dichloromethane under reduced pressure. Next, 24 g (0.16 mole) of sodium iodide and 200 g of acetone were placed in another 1-liter reactor and heated under reflux, and the above-described concentrated solution was added dropwise thereto. Thereafter, this mixture was stirred for 6 hours under reflux of acetone. After cooling, 400 g of purified water and 200 ml of n-hexane were added and the resulting mixture was allowed to separate into two layers. The organic layer was recovered, washed with 300 g of a 3% aqueous sodium thiosulfate solution and then 300 g of a 5% aqueous sodium chloride solution, freed of solvent, and distilled to obtain 29 g of a pale-yellow oily liquid having a boiling point of 116°–117° C./0.2 mmHg. On the basis of various spectral data, this product was identified as 1-iodo-cis-3-tetradecene (purity 92%, yield 82.8%).

The relationship between the spectral data of the 1-halo-cis-3-tetradecenes prepared in the foregoing Examples 1–3 and the various figures in the accompanying drawings is shown in Table 2 below.

TABLE 2

Figure 1:
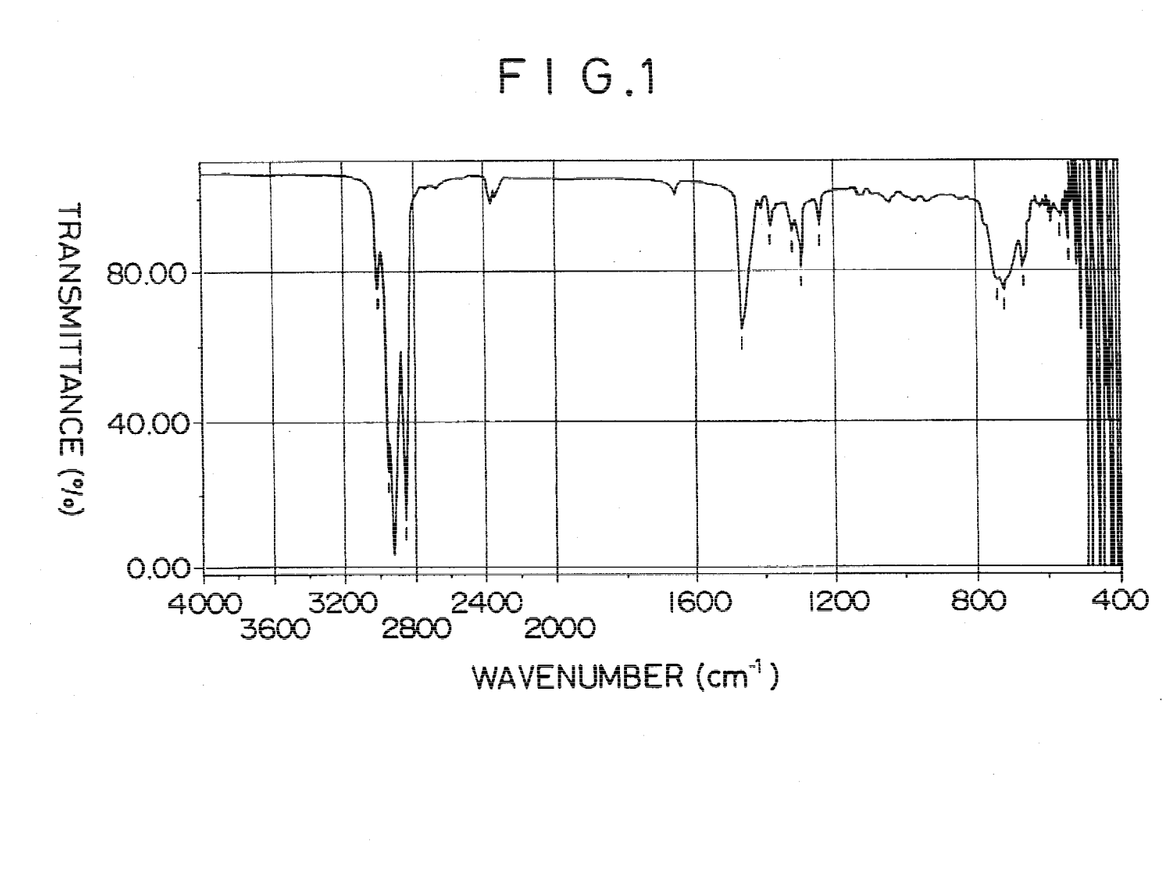
FIG. 1 is the infrared absorption spectrum of the 1-halo-cis-3-tetradecene prepared in Example 1.
Figure 2:
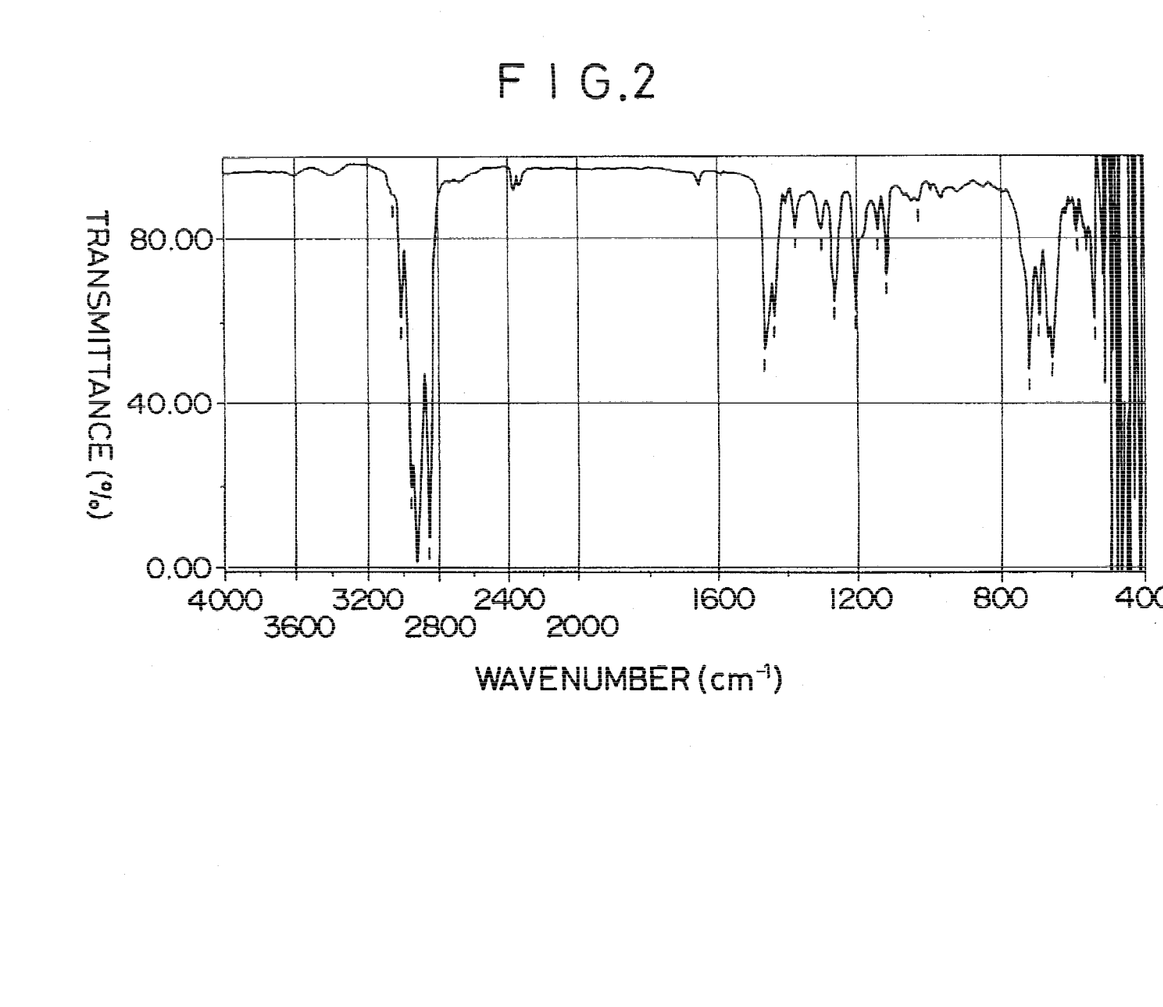
FIG. 2 is the infrared absorption spectrum of the 1-halo-cis-3-tetradecene prepared in Example 2.
Figure 3:
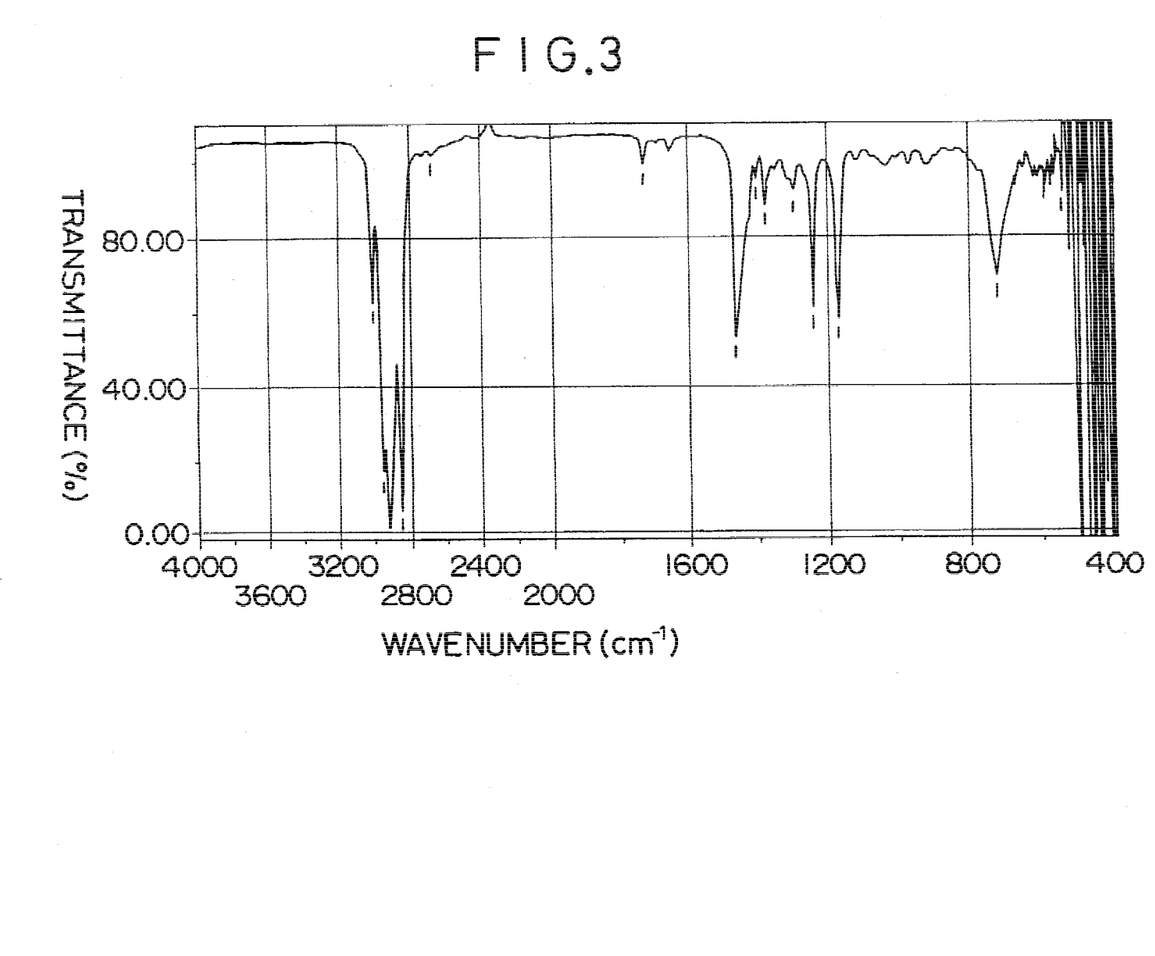
FIG. 3 is the infrared absorption spectrum of the 1-halo-cis-3-tetradecene prepared in Example 3.
Figure 4:
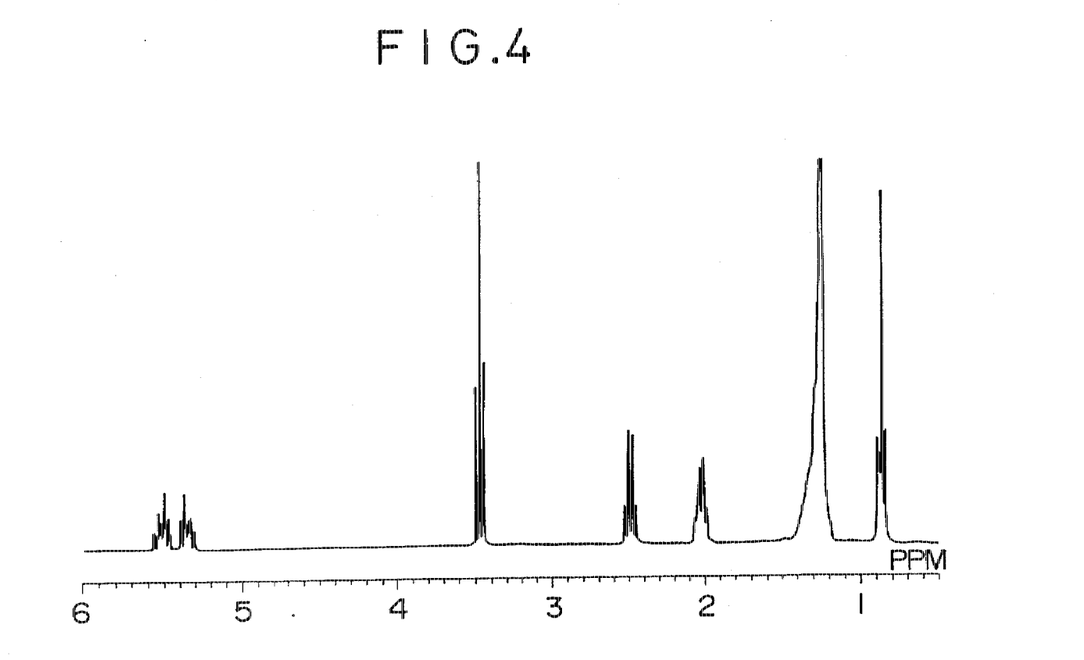
FIG. 4 is the $^1$H-nuclear magnetic resonance spectrum of the 1-halo-cis-3-tetradecene prepared in Example 1.
Figure 5:
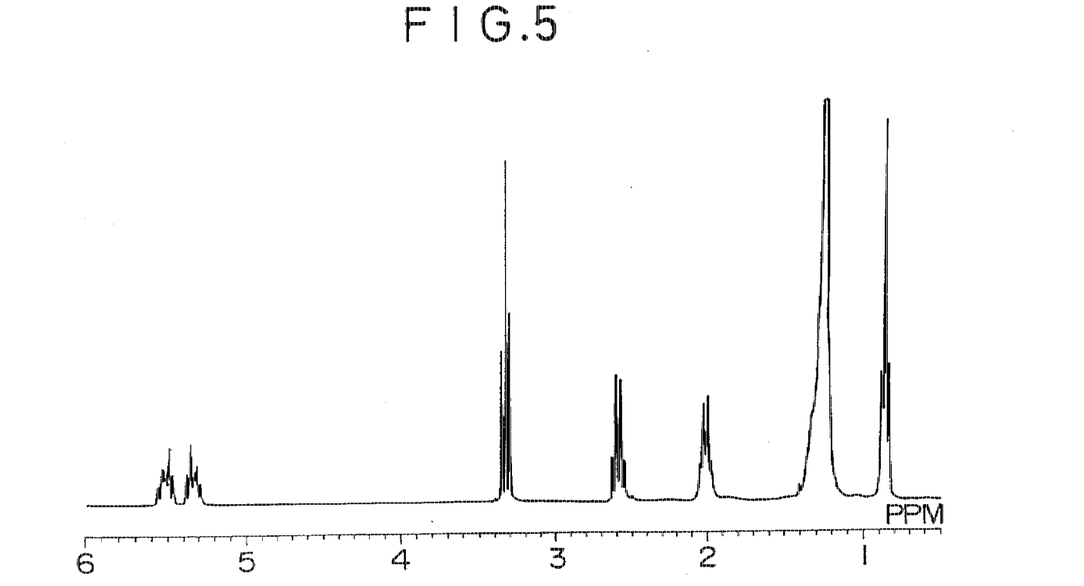
FIG. 5 is the $^1$H-nuclear magnetic resonance spectrum of the 1-halo-cis-3-tetradecene prepared in Example 2.
Figure 6:
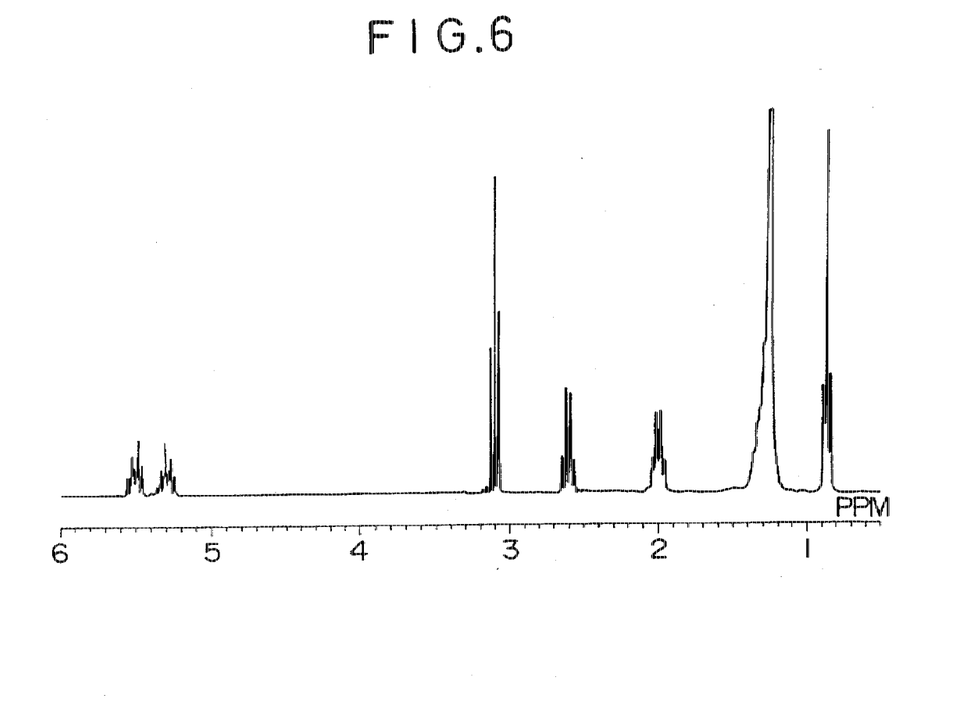
FIG. 6 is the $^1$H-nuclear magnetic resonance spectrum of the 1-halo-cis-3-tetradecene prepared in Example 3.
Figure 7:
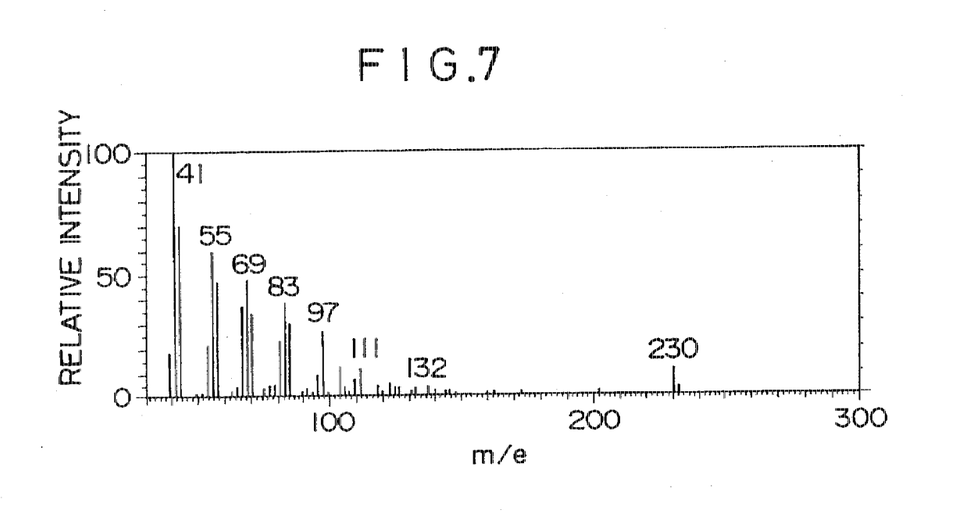
FIG. 7 is the mass spectrum of the 1-halo-cis-3-tetradecene prepared in Example 1.
Figure 8:
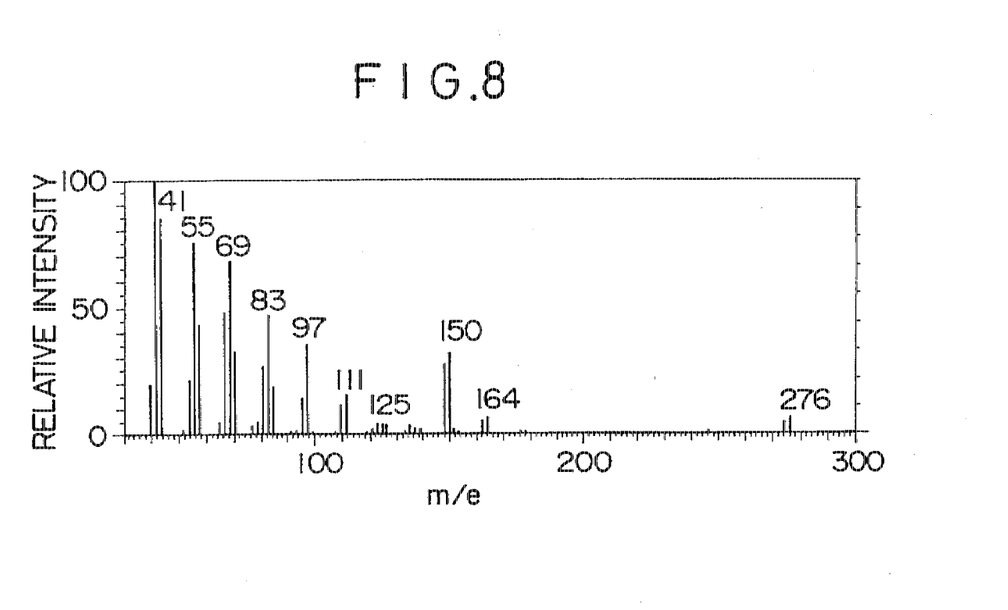
FIG. 8 is the mass spectrum of the 1-halo-cis-3-tetradecene prepared in Example 2.
Figure 9:
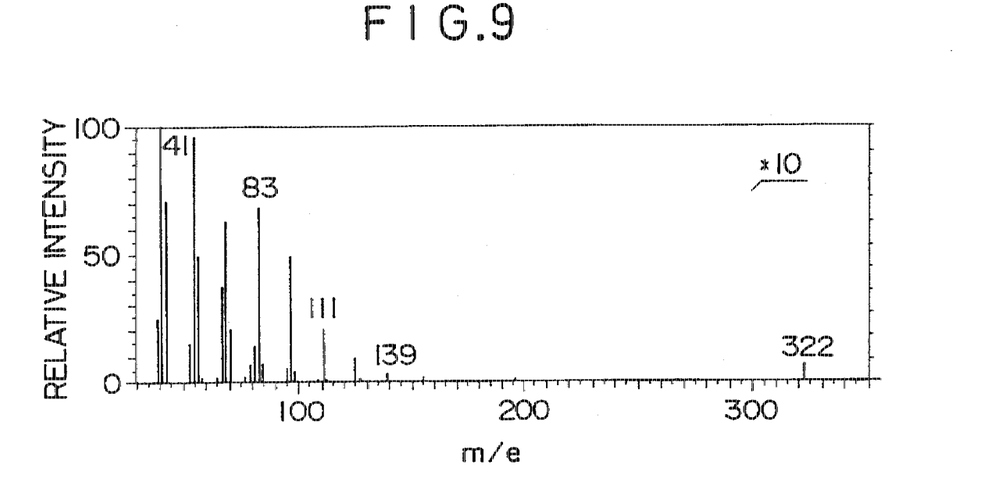
FIG. 9 is the mass spectrum of the 1-halo-cis-3-tetradecene prepared in Example 3.

| Spectral data | 1-Halo-cis-3-tetradecene | | |
|---|---|---|---|
| | X = Cl | X = Br | X = I |
| Infrared absorption spectrum | FIG. 1 | FIG. 2 | FIG. 3 |
| $^1$H-nuclear magnetic resonance spectrum | FIG. 4 | FIG. 5 | FIG. 6 |
| Mass spectrum (EI) | FIG. 7 | FIG. 8 | FIG. 9 |

EXAMPLE 4

Synthesis of cis-5-hexadecene (the copulation-inhibiting substance of the rice stem borer)

[Process 1 using a Grignard reagent]

A 1-liter reactor was charged with 5.0 g (0.206 mole) of magnesium and 90 g of tetrahydrofuran, and the reaction was initiated by adding 2 g of ethyl bromide and 46 g (0.2 mole) of 1-chloro-cis-3-tetradecene dropwise thereto under an atmosphere of nitrogen. After completion of the addition, the mixture was stirred for 2 hours under reflux of tetrahydrofuran and the resulting liquid was transferred to a 300-ml dropping funnel. Next, 30 g of tetrahydrofuran, 0.5 g of cuprous bromide and 22 g (0.204 mole) of ethyl bromide were placed in another 1-liter reactor and cooled to 0° C. Then, the above-described Grignard reagent was added dropwise thereto so that the temperature did not exceed 10° C. After completion of the reaction, 100 g of a saturated aqueous ammonium chloride solution was added and the resulting mixture was allowed to separate into two layers. The organic layer was recovered, freed of tetrahydrofuran under reduced pressure, and distilled to obtain 37.7 g of cis-5-hexadecene (purity 96%, yield 81%, b.p. 149°–152° C./3 mmHg). MS(m/e): 56(100%), 224 (M$^+$, 21%).

EXAMPLE 5

Synthesis of 2-methyl-cis-7-octadecene (a sex pheromone precursor of the gypsy moth)

[Process 1 using a Grignard reagent]

In a 1-liter reactor, a Grignard reagent was prepared from 5.0 g (0.206 mole) of magnesium and 46 g (0.2 mole) of 1-chloro-cis-3-tetradecene in exactly the same manner as in Example 4. Next, 30 g of tetrahydrofuran, 30 g (0.2 mole) of isoamyl bromide and 0.6 g of cuprous iodide were placed in another 1-liter reactor and cooled to 0° C. Then, the above-described Grignard reagent was added dropwise thereto so that the temperature did not exceed 20° C. After completion of the reaction, the reaction product was distilled in exactly the same manner as in Example 4 to obtain 20 g of 2-methyl-cis-7-octadecene (purity 96.0%, yield 77%, b.p. 155°–158° C./2 mmHg). MS(m/e): 56(100%), 266 (M$^+$, 27%).

EXAMPLE 6

Synthesis of cis-10-henicosene (a sex pheromone component of *Drosophila virlis*)

[Process 2 using a Grignard reagent]

A 1-liter reactor was charged with 5.0 g (0.206 mole) of magnesium and 150 g of tetrahydrofuran, and the reaction was initiated by adding a piece of bromine and 35.6 g (0.2 mole) of n-heptyl bromide dropwise thereto under an atmosphere of nitrogen. After completion of the addition, the mixture was stirred for 2 hours under reflux of tetrahydrofuran and the resulting liquid was transferred to a 300-ml dropping funnel. Next, 30 g of tetrahydrofuran, 0.4 g of cuprous chloride and 49.5 g (0.18 mole) of 1-bromo-cis-3-tetradecene were placed in another 1-liter reactor and cooled to 0° C. Then, the above-described Grignard reagent was added dropwise thereto so that the temperature did not exceed 10° C. After completion of the reaction, 100 g of a saturated aqueous ammonium chloride solution was added and the resulting mixture was allowed to separate into two layers. The organic layer was recovered, freed of tetrahydrofuran under reduced pressure, and distilled to obtain 22.3 g of cis-10-henicosene (purity 95.1%, yield 75%, b.p. 171°–175° C./2 mmHg). MS(m/e): 56(100%), 294 (M$^+$, 10%).

EXAMPLE 7

Synthesis of cis-9-icosene (the response-stimulating substance of *Drosophila virlis*)

[Process2 using lithium]

A 500-ml reactor was charged with 100 ml of diethyl ether and 0.7 g (0.1 mole) of lithium pieces under an atmosphere of nitrogen. When 8.2 g (0.05 mole) of 5-hexyl bromide was added dropwise thereto at 20°–25° C., the mixture became turbid. This mixture was stirred at 10° C. for several minutes and then allowed to stand, and the resulting supernatant was withdrawn with a syringe. Next, 50 ml of diethyl ether and 4.5 g (0.023 mole) of cuprous iodide were placed in another 200-ml reactor and cooled to −20° C. After the addition of the above-described supernatant, the mixture was stirred at for about an hour and then allowed to stand, and the resulting supernatant was again withdrawn with a syringe. Next, 20 ml of diethyl ether and 3.2 g (0.01 mole) of 1-iodo-cis-3-tetradecene were placed in another 500-ml reactor. The above-described supernatant was slowly added thereto at −20° C., followed by stirring for 4 hours. After completion of the reaction, 50 g of a saturated aqueous ammonium chloride solution was added and the solvent was removed under reduced pressure. By subjecting the residue to silica gel chromatography, 1.76 g of cis-9-icosene (purity 95.8%) was recovered. MS(m/e): 56(100%), 280 (M$^+$, 8%).

EXAMPLE 8

Synthesis of 2-methyl-cis-7-octadecene (a sex pheromone precursor of the gypsy moth)

[Process 1 using a Grignard reagent]

In a 1-liter reactor, a Grignard reagent was prepared from 5.0 g (0.206 mole) of magnesium and 46 g (0.2 mole) of 1-chloro-cis-3-tetradecene in exactly the same manner as in Example 4. Next, 100 g of tetrahydrofuran, 45.2 g (0.2 mole) of isoamyl p-toluenesulfonate and 0.5 g of cuprous iodide were placed in another 1-liter reactor and cooled to −20° C. Then, the above-described Grignard reagent was added dropwise thereto. After completion of the reaction, the mixture was stirred at 0° C. for 2 hours and then stirred without cooling until the temperature rose gradually to room temperature. Then, 100 g of a saturated aqueous ammonium chloride solution was added and the resulting mixture was allowed to separate into two layers. The organic layer was recovered and freed of solvent under reduced pressure. The resulting was distilled to obtain 16.1 g of 2-methyl-cis-7-octadecene (purity 96.0%, yield 62%, b.p. 155°–158° C./2 mmHg). MS(m/e): 56(100%), 266 (M$^+$, 27%).

We claim:

1. A process for the preparation of cis-olefin compounds for the which comprises converting a compound of the formula RX$^b$ wherein R is an alkyl group and X$^b$ is a halogen atom, into an organometallic compound RM$^b$ wherein M$^b$ is a metal atom or MgX$^b$, and reacting the organometallic compound RM$^b$ with a cis compound of the formula (IV)

$$CH_3(CH_2)_9CH=CH(CH_2)_2Z \qquad (IV)$$

wherein Z is a bromine or iodine atom, to form a cis-olefin compound of the formula (V)

$$CH_3(CH_2)_9CH=CH(CH_2)_2R \qquad (V)$$

wherein R is as previously defined.

2. A process for the preparation of cis-olefin compounds which comprises converting a compound having the formula $$CH_3(CH_2)_9CH=CH(CH_2)_2X^a \qquad (I)$$

wherein X$^a$ is selected from the group consisting of chlorine, bromine, and iodine, into an organometallic compound of the formula (II)

$$CH_3(CH_2)_9CH=CH(CH_2)_2M^a \qquad (II)$$

wherein M$^a$ is a metal atom or MgX$^a$ in which X$^a$ is a halogen atom, and reacting the organometallic compound with a compound of the general formula RY wherein R is an alkyl group and Y is a bromine atom, iodine atom, tosyloxy group or mesyloxy group, to form a cis-olefin compound of the formula $$CH_2(CH_2)_9CH=CH(CH_2)_2R \qquad (III)$$

wherein R is as previously defined.

* * * * *